United States Patent
Carman et al.

(10) Patent No.: US 7,200,458 B2
(45) Date of Patent: Apr. 3, 2007

(54) WOOD TRACKING BY IDENTIFICATION OF SURFACE CHARACTERISTICS

(75) Inventors: George M. Carman, Corvallis, OR (US); Patrick S. Freeman, Corvallis, OR (US); Ofer Heyman, Corvallis, OR (US); William J. Briskey, Monmouth, OR (US)

(73) Assignee: Lucidyne Technologies, Inc., Corvallis, OR (US)

( * ) Notice: Subject to any disclaimer, the term of this patent is extended or adjusted under 35 U.S.C. 154(b) by 48 days.

(21) Appl. No.: 10/898,668

(22) Filed: Jul. 23, 2004

(65) Prior Publication Data
US 2005/0040085 A1 Feb. 24, 2005

Related U.S. Application Data

(60) Provisional application No. 60/489,862, filed on Jul. 24, 2003.

(51) Int. Cl.
*G06F 19/00* (2006.01)
*B07C 5/14* (2006.01)

(52) U.S. Cl. .................... 700/117; 700/115; 700/167; 209/517

(58) Field of Classification Search ............... 700/117, 700/167; 209/517–521; 382/141; 144/402–403
See application file for complete search history.

(56) References Cited

U.S. PATENT DOCUMENTS

| | | | |
|---|---|---|---|
| 4,086,496 A | 4/1978 | Berry | 250/561 |
| 4,207,472 A | 6/1980 | Idelsohn et al. | 250/563 |
| 4,221,974 A | 9/1980 | Mueller et al. | 250/563 |
| 4,286,880 A | 9/1981 | Young | 356/431 |
| 4,301,373 A | 11/1981 | Sjödin | 250/560 |
| 4,606,645 A | 8/1986 | Matthews et al. | 356/446 |
| 4,827,142 A | 5/1989 | Hatje | 250/563 |
| 4,831,545 A | 5/1989 | Floyd et al. | 364/507 |
| 4,867,213 A | 9/1989 | Bolton et al. | 144/357 |
| 4,879,752 A | 11/1989 | Aune et al. | 382/1 |
| 4,916,629 A | 4/1990 | Bogue et al. | 364/507 |
| 4,926,350 A | 5/1990 | Bechtel et al. | 364/550 |
| 4,992,949 A | 2/1991 | Arden | 364/478 |
| 5,252,836 A | 10/1993 | Matthews et al. | 250/571 |
| 5,254,859 A | 10/1993 | Carman et al. | 250/560 |
| 5,412,220 A | 5/1995 | Moore | 250/563 |

(Continued)

FOREIGN PATENT DOCUMENTS

FR        2 797 975        9/1999
WO        WO 03/019308 A1  3/2003

OTHER PUBLICATIONS

A rough (nonprofessional) English translation of French Patent No. 2 797 975, dated Jan. 9, 1999, that was submitted with the last IDS.

(Continued)

*Primary Examiner*—Alexander Kosowski
(74) *Attorney, Agent, or Firm*—Stoel Rives LLP

(57) ABSTRACT

A "woodprint™" characterization and identification technique unique employs cameras (16), lighting (14), camera interface hardware (18), a computer (20), and/or image processing software to collect and analyze surface characteristics of pieces of wood (8) to track them through an automated production process in real-time with information that is specific to each wood piece (8), such as what machining is required, its value, and/or its destination. When a wood piece (8) reaches a point in the production process where a decision is required, its unique identity is used to retrieve appropriate information previously determined and assigned to the wood piece (8).

69 Claims, 4 Drawing Sheets

U.S. PATENT DOCUMENTS

| | | | | |
|---|---|---|---|---|
| 5,421,385 | A | | 6/1995 | McGee .................. 144/357 |
| 5,518,052 | A | | 5/1996 | Westberg et al. ........... 144/398 |
| 5,524,771 | A | | 6/1996 | Kairi et al. ................. 209/518 |
| 5,544,256 | A | * | 8/1996 | Brecher et al. ............ 382/149 |
| 5,544,757 | A | * | 8/1996 | Geiger et al. ............... 209/518 |
| 5,644,392 | A | | 7/1997 | Soest ........................ 356/237 |
| 5,703,960 | A | | 12/1997 | Soest ........................ 382/141 |
| 5,710,835 | A | | 1/1998 | Bradley ..................... 382/233 |
| 5,960,104 | A | * | 9/1999 | Conners et al. ............ 382/141 |
| 6,031,567 | A | * | 2/2000 | Johnson ..................... 348/91 |
| 6,272,437 | B1 | | 8/2001 | Woods et al. ................ 702/35 |
| 6,756,789 | B1 | | 6/2004 | Parker et al. ............... 324/637 |
| 6,757,058 | B1 | | 6/2004 | Carman et al. .......... 356/237.2 |
| 6,813,927 | B1 | * | 11/2004 | Harris et al. .............. 73/12.12 |
| 7,004,329 | B2 | * | 2/2006 | Magnan ..................... 209/517 |
| 2003/0079544 | A1 | | 5/2003 | Floyd ........................ 73/597 |
| 2003/0192412 | A1 | | 10/2003 | Otto et al. ..................... 83/13 |
| 2005/0013472 | A1 | * | 1/2005 | Gauthier ..................... 382/141 |

OTHER PUBLICATIONS

International Search Report concerning corresponding International Application No. PCT/US2004/023727.

Written Opinion concerning corresponding International Application No. PCT/US2004/023727.

Richard W. Conners, D. Earl Kline, Philip A. Araman, and Thomas H. Drayer, *IEEE* (Jul. 1997), 43-48, "Machine Vision Technology for the Forest Products Industry".

* cited by examiner

WOOD TRACKING BY IDENTIFICATION OF SURFACE CHARACTERISTICS

RELATED APPLICATIONS

This patent application derives priority from U.S. Provisional Application No. 60/489,862, filed Jul. 24, 2003.

COPYRIGHT NOTICE

© 2004 Lucidyne Technologies, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71 (d).

TECHNICAL FIELD

The present invention relates generally to lumber or board tracking and, more particularly, to using unique surface characteristics ("woodprints") for identifying individual pieces of wood and tracking them through an automated production process with real-time information specific to the pieces or wood such that when a board or other piece of wood reaches a machining operation or decision point, its predetermined characteristic information, such as processing information, value, or destination, can be automatically retrieved to influence how such piece of wood is handled.

BACKGROUND OF THE INVENTION

Conventional board tracking devices rely on spraying or imprinting an identification code or symbol on each board and reading the information with a sensor after the board has traveled to a subsequent machining station. The printing and reading processes are preferably performed at high speeds and may be physically difficult to reliably achieve because of the dynamic nature of the boards themselves.

If wood is missing from an area where the board is printed, the board's identification code can be illegible to the reader. A twisted board, or one with bark or some other defect in the print zone, can also be difficult to reliably mark and identify. A board may also turn over during travel between stations, requiring that either both sides be marked, or both sides be read.

Another problem with conventional board tracking devices is that printing systems contain print media, such as ink or paint, and moving parts that contribute to decreasing reliability. Ink jet and/or spray systems require constant maintenance to keep them working properly. Most require compressed air, are adversely affected by temperature extremes, and are very sensitive to variations in the ink or paint quality. For example, unless the print media is continually circulated when the system is not in use, the print media can freeze, its pigments can separate, and print nozzles can become plugged. The required maintenance can cost thousands of dollars annually beyond the cost of replacement parts and the original equipment itself. When a marking system fails, the failure is typically not detected until the boards reach the next machine center, potentially meaning that a hundred or more boards must be physically removed from the process and either reintroduced ahead of the marking system or manually processed.

Marking boards with ink or paint can reduce their value as potential appearance-grade products destined for exposed applications. Boards typically processed through a marking system have been previously planed and are ready for immediate use. Some uses include wall paneling or exposed ceilings and floors. If the final finish will be a non-opaque stain or paint, any non-natural marking will not be acceptable. Furthermore, print media typically contain or are mixed with a fluorescent pigment or dye to provide better contrast to improve mark-reading performance. Such pigments may be invisible in normal lighting, but the marks will glow under an ultraviolet (black light) source. The ultraviolet marks are, therefore, unacceptable for applications where the surfaces are inadvertently illuminated by a lighting source that emits UV light.

While existing board tracking systems may be suitable for some specific purposes, a more universal method for tracking boards, regardless of their condition or their final application, is desirable.

SUMMARY OF THE INVENTION

An object of the present invention is, therefore, to provide an improved wood tracking system.

Another object of the invention is to provide a surface "woodprinting™" system and/or method for tracking pieces of wood.

An alternative object of the invention is to employ such woodprinting™ capabilities to identify individual pieces of wood using their unique inherent surface characteristics in order to track the wood in real-time through an automated production process.

Another alternative object of the invention is to provide woodprinting™ capabilities that identify each piece of wood by its unique grain characteristics.

A further alternative object of the invention is to provide woodprinting™ capabilities that do not mark or modify the wood surface or its appearance.

Yet another alternative object of the invention is to provide woodprinting™ capabilities that can be used on any face, edge, and/or end of surfaced or unsurfaced wood of any moisture content.

Still another alternative object of the invention is to provide woodprinting™ capabilities that are relatively insensitive to lighting or positioning differences during image data collection.

As with human fingerprints and snowflakes, wood cells in trees develop in distinct manners as a result of many factors, including genetics, environment, weather, soil, local life form effects, and many other contributing elements. The surface of an individual board or piece of wood can also be cut from a tree in an infinite number of angles. Accordingly, the resulting exposed grain structure of any given surface will be unique when compared to that of any other surface of any other piece of wood. Even boards taken from the same tree and cut at similar angles will have unique grain structures. Furthermore, if the piece of wood is twisted, has some bark, is missing wood, has other physical shape defects such as wane defects, or has other defects such as knots or pitch, within an area of interest, these features become additional characteristics that can be used to uniquely identify the piece of wood.

Some embodiments provide a surface "boardprint™" or "woodprint™" identification technique for identifying individual pieces of wood using their inherent unique surface characteristics to track them in real time through an automated production process. Such embodiments overcome many of the disadvantages of conventional board tracking devices. The improved tracking technique permits information specific to a piece of wood, such as proposed machining information, value, destination, and/or other characteristics, to follow the individual piece of wood through an automated process. Thus, when the piece of wood reaches a point in a production process where a decision is desired, the unique identity of the wood piece can be used to retrieve the appropriate information already associated with it.

Some embodiments employ cameras, lighting, image acquisition hardware, a computer, and image processing software. Preferred processing algorithms reduce effects from random or varying angles of image collection and/or from fluctuations of lighting sources. Statistical parameters, conceptually similar to those used for human fingerprint matching technology, provide a certain amount of flexibility in the analytical process. So, as long as a piece of wood meets desired statistical requirements for a match, the wood piece is considered to be a match. An adjustable tolerance for accuracy can be employed to compensate for fluctuations in the readability of wood grain characteristics, for example. These techniques are unlike conventional wood tracking techniques that attempt to find an exact match for a printed code.

Preferred image processing techniques of the invention can be used on any face, edge, and/or end of surfaced or unsurfaced wood of any moisture content, such as green (uncured) or dry wood, and the image processing techniques are relatively insensitive to defects on the surfaces. So, unlike convention tracking systems which cannot track relatively green or unsurfaced boards that do not facilitate the use of print media, embodiments of a woodprint™ identification system can be used anywhere in a sawmill and/or planer mill process where a wood surface can be imaged and is not limited to use with dry, surfaced boards. Furthermore, since printing or stamping the boards can be eliminated and the image acquisition sensors do not need to contact the wood surfaces, the wood is left with no additional markings that could degrade its appearance or adversely affect its value or merchantability.

Preferred embodiments of the invention can be employed to work in conjunction with an automated wood grading system. Because the scanning and computer processing associated with automated board or lumber grading may take several seconds, boards may travel away from the scanner and be mixed in with subsequent or previous boards without adversely affecting throughput. The woodprint™ identification techniques therefore facilitate automated matching of grade solutions with correct boards or other pieces of wood when they are presented later for further machining.

Some preferred embodiments can be implemented without adding appreciably to the production cost of wood products. Some preferred embodiments employ no moving parts and utilize components that are easily protected from temperature fluctuation and other environmental concerns. Some preferred embodiments can also utilize existing scanning hardware for initial image acquisition in existing systems, merely adding a software element to the scanning system. Off-the-shelf lighting, cameras, and/or other sensing hardware can be added downstream at various points in the automated production system. The expected maintenance, such as keeping the camera viewing ports free from debris, and occasionally replacing of light sources, would also be minimal. Accordingly, the preferred surface woodprinting™ techniques for tracking wood pieces is highly reliable.

Additional objects and advantages of this invention will be apparent from the following detailed description of preferred embodiments, which proceeds with reference to the accompanying drawings.

DETAILED DESCRIPTION OF PREFERRED EMBODIMENTS

Figure 1:
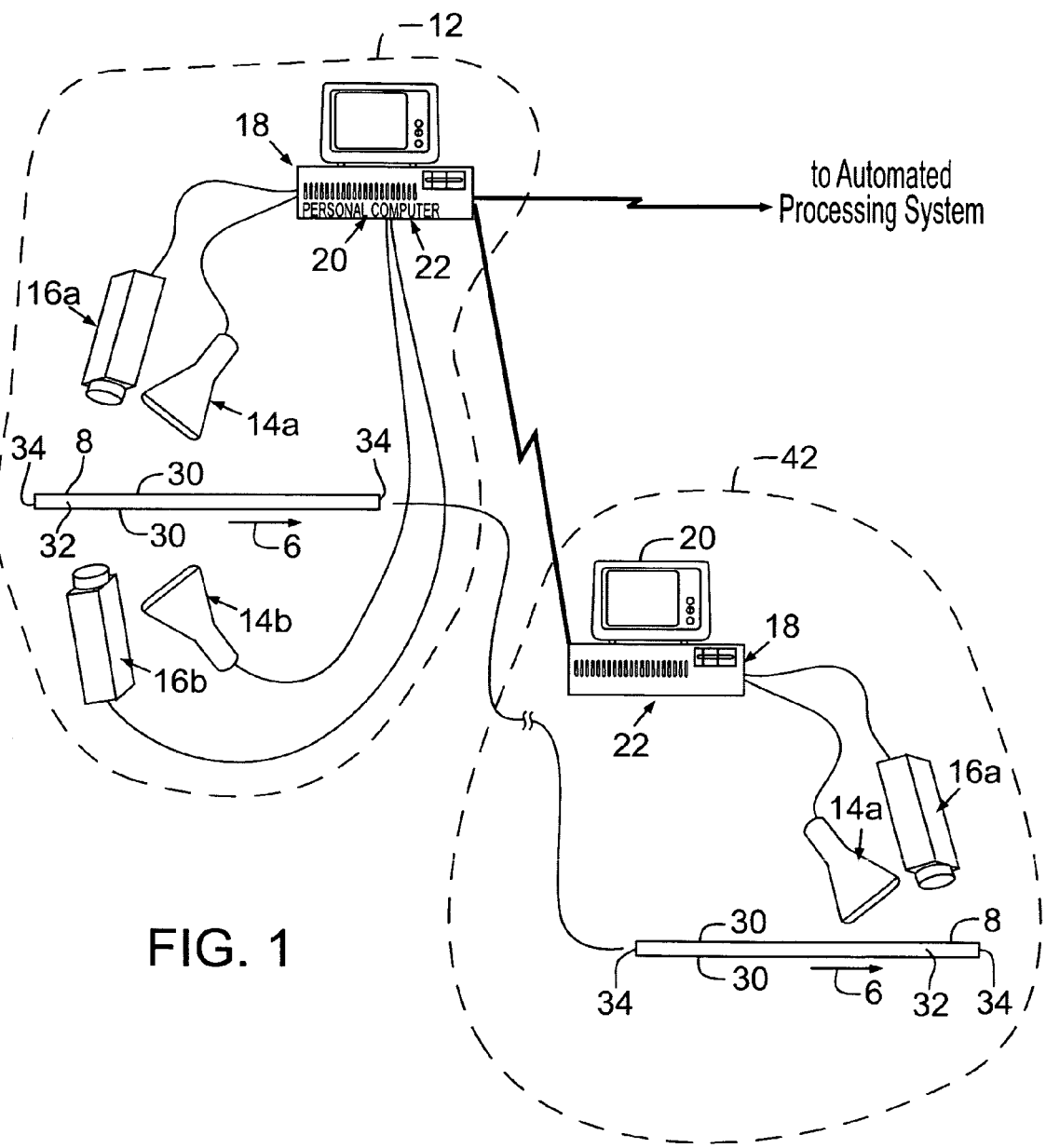
FIG. 1 is a pictorial representation of exemplary desirable components of one embodiment of a wood tracking system.
Figure 2:
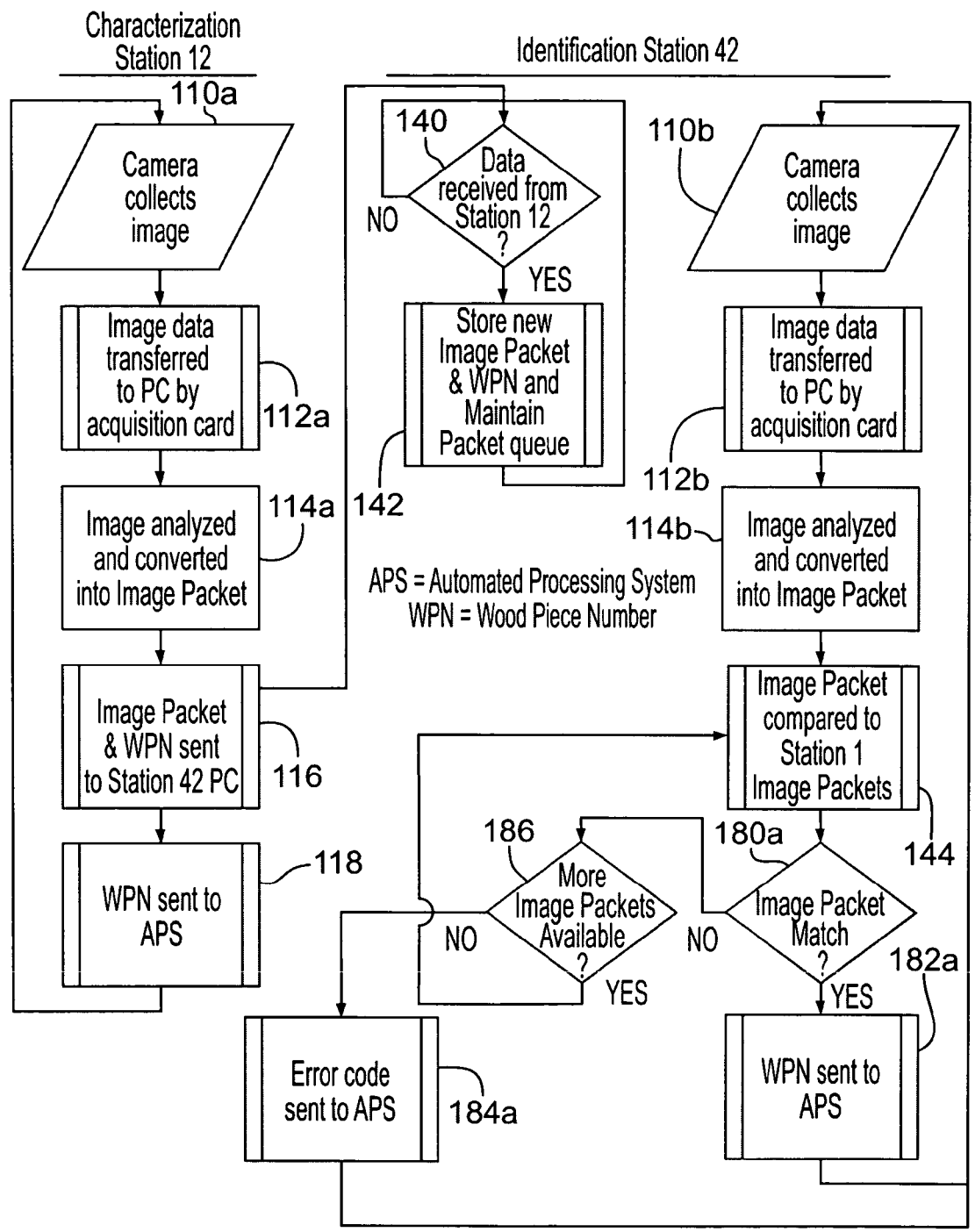
FIG. 2 is a flow diagram of an overview of exemplary wood tracking events that occur in one embodiment of a wood tracking system.
Figure 3:
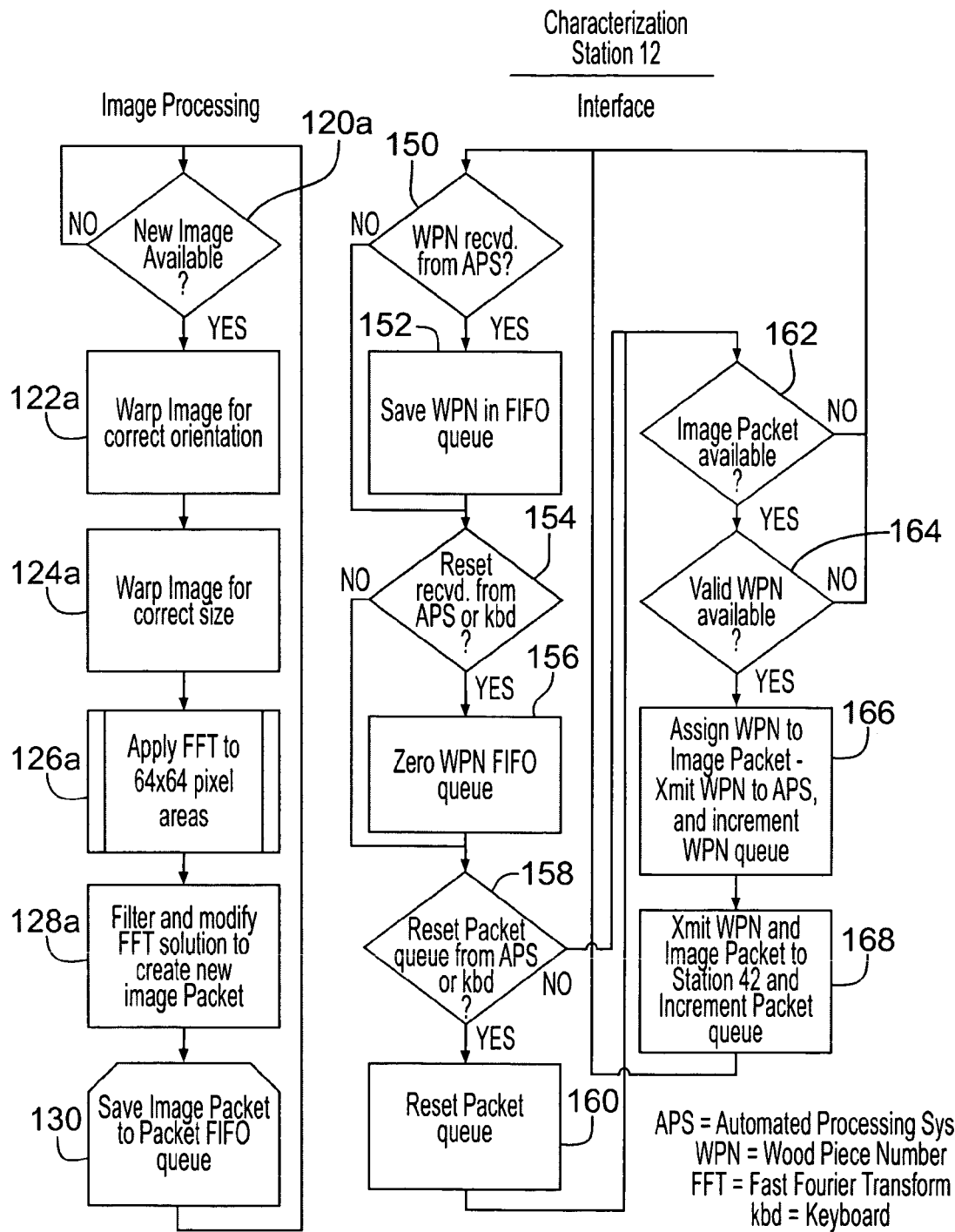
FIG. 3 is a flow diagram detailing exemplary image analysis executed at an exemplary characterization station in one embodiment of a wood tracking system.
Figure 4:
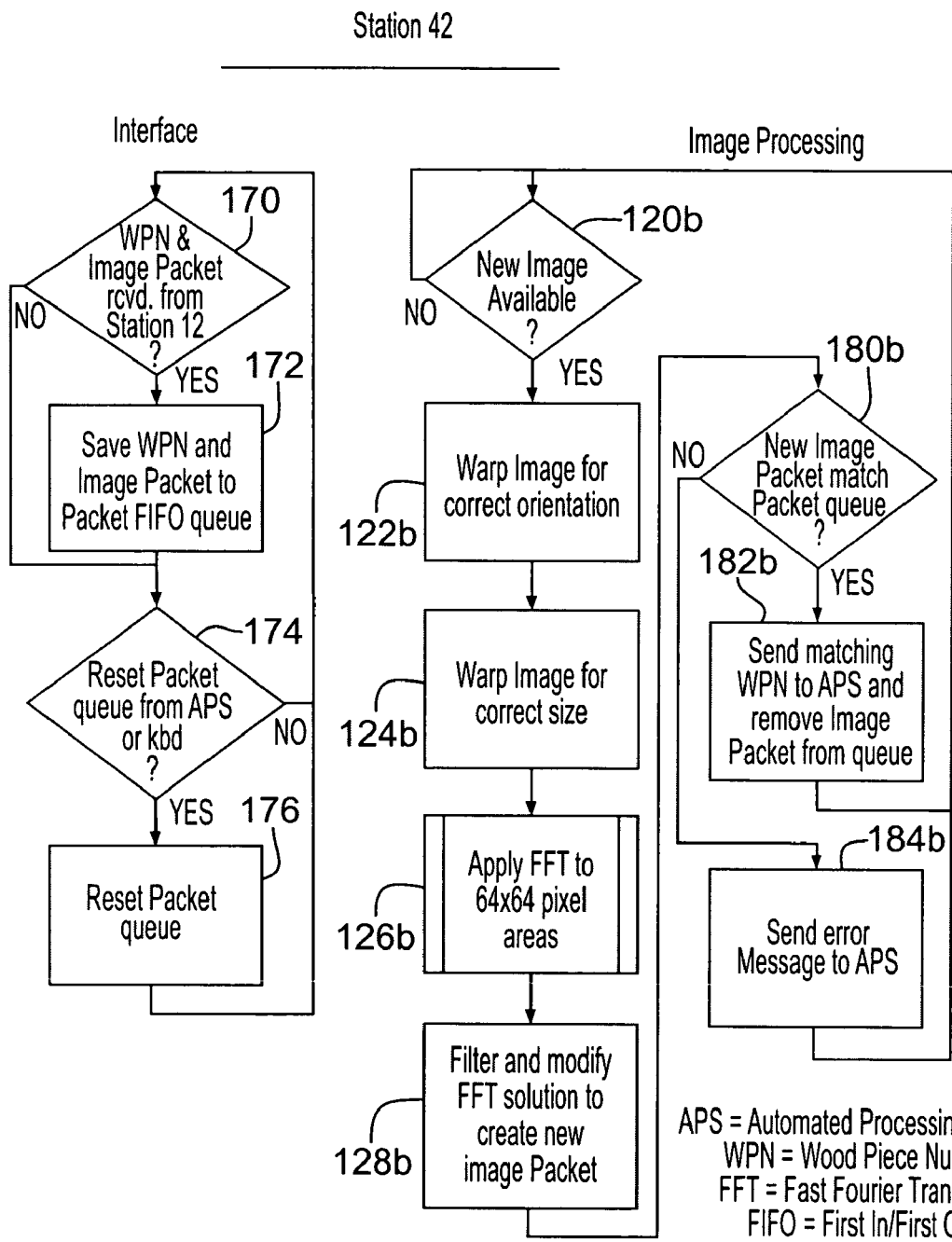
FIG. 4 is a flow diagram detailing exemplary image analysis executed at an exemplary identification station in one embodiment of a wood tracking system.

FIG. 1 shows an exemplary wood tracking system 10 for characterizing and identifying pieces of wood 8 in a production line as they move in a direction of travel 6 through an automated production process to downstream processing centers and/or sorting bins. FIGS. 2–4 show general and specific flow diagrams of wood tracking events and analysis employed in some embodiments of wood tracking system 10.

With reference to FIG. 1, a characterization station 12 captures and processes an image of at least a portion of each piece of wood 8 and then coordinates the tracking of the specific pieces of wood 8 with the automated processing system (APS) as they travel to common or different machining centers for the sawing, grading, and/or subsequent sorting. The pieces of wood 8 can flip over during travel or arrive at the machining centers out of sequence. A downstream identification station 42 at one or more of such machining centers eventually captures and processes the images of most, if not all, the pieces of wood 8. Then image data obtained at the identification station 42 is compared to image data obtained at the station 12 to identify each piece of wood 8 and report its location to the automated processing system. Each piece of wood 8 is then processed or sorted according to wood piece-specific instructions from the automated process system. After being processed, each piece of wood 8 may be re-characterized by the original characterization station 12 or another characterization station 12 that is downstream of such processing or machining center.

General embodiments of a wood tracking system 10 include one or more wood characterization stations 12 having one or more light sources 14a and 14b (generically light sources 14) and corresponding image acquisition hardware 16a and 16b (generically image acquisition hardware 16) that are directly or indirectly in communication with camera interface hardware 18 that is in turn directly or indirectly in communication with a computer 20. A typical wood characterization station 12 also preferably employs image processing software 22 having customized image processing algorithms designed to analyze video, frame, or other captured image information using various data manipulation techniques described later in detail.

Enough unique inherent information can be extracted from a small surface portion of each piece of wood 8 as it travels at a high speed through the characterization station 12 to successfully characterize each piece of wood 8 uniquely. Typically, pieces of wood 8 travel (with their major axis in the direction of travel 6 (lineally)) through station 12 at speeds of about 91 to 910 meters (300 to 3000 feet) per minute and more typically at speeds of at least 366 meters (1200 feet) per minute and less than about 610 meters (2000 feet) per minute. In some embodiments, a roughly 61-centimeter (two-foot) surface portion that is about one meter (three feet) from the end of each piece of wood 8 is imaged at station 12.

For convenience, the terms "wood," "pieces of wood," or "wood pieces" may refer to pieces of timber, lumber, logs, flitches, cants, beams, posts, studs, boards, veneer, and/or any other pieces of wood smaller than the whole tree and larger than sawdust. The surfaces characterized may be one or more faces 30, sides 32, and/or ends 34 of the wood pieces 8. Skilled persons will appreciate that curved or intersecting surfaces may additionally or alternatively be characterized at station 12. Skilled persons will appreciate that the minimum area that is imaged should be an amount of area sufficient to yield a unique recognizable vector file or image packet as later described. Skilled persons will further appreciate that the minimum area imaged may be different for different wood products or may be different for wood pieces having different shapes or sizes. Alternatively, any additional amount of any wood surface can be imaged, including up to all portions of all surfaces. Skilled persons will also note that any combination of surfaces may also be imaged.

In some embodiments, the image captured comprises a high contrast image of grain and/or growth ring characteristics of a portion of each piece of wood 8. These features are relatively insensitive to differences in lighting, position, and contrast, but other wood characteristics such as tracheid patterns and/or wood defects could be used for identification purposes. Such defects might include, but are not limited to, physical shape defects such as cups, crooks, cracks, knots, wane, twists, bark, and/or pitch.

Although only a portion of one surface of each piece of wood 8 may be characterized at the characterization station 12, images of portions of opposite surfaces may also be collected at the characterization station 12 so that opposite surface information is available in the event that a piece of wood 8 is turned over in transit between the characterization station 12 and the identification station 42. Accordingly, the image acquisition hardware 16 and the respective lighting sources 14 may be mounted in such a way as to obtain images of portions of opposing surfaces of each piece of wood 8 as it travels through station 12.

Appropriate gaps may be provided between conveyor belts or other wood conveying means to permit viewing of the bottom surface of each piece of wood 8. In alternative embodiments, the sets of image acquisition hardware 16 and light sources 14 may be symmetrically positioned about opposite surfaces of wood pieces 8 to characterize opposite surfaces simultaneously or may be positioned at a distance so that the opposite surfaces are characterized sequentially. Alternatively, pieces of wood 8 may intentionally be flipped over and resent through a station 12 having only a single set of lighting sources 14 and image acquisition hardware 16 to characterize an opposite surface, or the image acquisition hardware 16 could be moved such that its field of view changed to include the opposite surface. However, such embodiments might entail additional safeguards to ensure that images of the opposite surfaces are properly correlated with each other. The images or image data collected at station 12 from some or all of the surfaces may be communicated to the same computer 20 for processing.

In one embodiment, process blocks 110*a* and 110*b* employ image acquisition hardware 16 that comprises one or more monochrome array cameras with at least about a 1024×768 pixel addressability. Such camera(s) can be configured to be electronically shuttered up to at about at least 7.5 frames/second with an adjustable integration time to include 500 microseconds, or such camera(s) can be configured to work with a strobed light source 14 having similar strobe frequencies. In an exemplary embodiment, a camera is positioned a minimum of 61 centimeters (24 inches) over a face 30 of a target piece of wood 8 to provide a minimum field of view of 36 centimeters by 61 centimeters (14 inches by 24 inches) using a fixed lens. Skilled persons will appreciate that the camera speed and resolution can vary depending on the speed of the production line and the maximum field of view desired.

One or more filters (not shown) may be added to reduce or eliminate infra-red energy and all visible wavelengths except green because most wood features of interest provide better visible contrast in green wavelengths. One or more filters may also be added to reduce or eliminate other unwanted characteristics of ambient lighting to enhance desirable effects of the light source(s) 14. The image acquisition hardware 16, and/or any other sensitive components as appropriate, may be housed in a NEMA 12/13-rated enclosure to protect it from temperature extremes, dust, and dirt. All of the components described above are commercially available.

In an alternative embodiment in which the wood piece 8 is a board, a Sony™ XCD-X700 color camera is mounted about 1.5 meters (five feet) above the face 30 of the board and is preferably oriented substantially perpendicularly to the board. The camera is installed in a NEMA 12/13-rated enclosure. The camera has a Fire Wire serial communication port, and a Fire Wire extender converts the Fire Wire signal to propagate through a fiber optic medium over a longer distance than the camera's own circuitry permits. Only the green color channel from the camera is used, and the background behind the board is preferably dark to facilitate image collection. The image acquisition cycle is triggered by a photoeye proximity transition sensor that detects the end 34 or edge 32 of the board, depending on the orientation of the board as it travels through station 12. Software running in the camera automatically transmits the acquired data to a personal computer 20.

In another embodiment, one or more color high-speed line scan cameras, having separate red, blue, and green channels, capture an image from a surface as a piece of wood 8 moves through station 12. The image data from the green channel is pieced back together to create an array image for subsequent analysis with software tools. In another embodiment, a single 768×768 pixel monochrome camera is employed to capture an image of an end 34 of a piece of wood 8 in a field of view of approximately 36 centimeters by 36 centimeters (14 inches by 14 inches) at the first station 12. It is desirable to capture a high quality image, but the particular method of image data capture employed may not be particularly relevant. Skilled persons will appreciate that successful image collection is not limited to using imaging techniques described above and that numerous types of image acquisition hardware are commercially available and numerous configurations and positions could be employed. For example, other color or black and white image data may be obtained, or even radio or other frequency data may be obtained and used for "image matching."

Skilled persons will appreciate that image acquisition hardware may take on many other forms. In one embodiment, photodiodes are employed to capture inherent characteristic information obtained from exposing the wood pieces 8 to x-ray radiation. In another embodiment, antennas are employed to capture inherent characteristic information obtained from exposing the pieces of wood 8 to radio waves.

Light sources 14 may employ almost any commercially available lighting equipment or known lighting technique. Desirable light sources 14 provide wavelengths generally considered to be green light at sufficient energy to accommodate the integration time necessary to capture well-contrasted images. Too much light is not likely to be a problem since the camera aperture or integration time can be adjusted to compensate for excess intensity. Although light sources 14 with reflector and lens systems that project a visible intensity pattern onto a wood surface can be employed, lighting embodiments that do not project visible intensity pattern onto a wood surface are generally easier to implement. In one embodiment, station 12 employs one or more a broad-spectrum lamps, such as commercially available halogen or Xenon lamps that consume about 1000 Watts of direct current (DC) power to generate approximately 800 Watts of light energy. The lamp's self-contained lens and reflector cast a diffuse light over an approximate area of about 76 centimeters by 76 centimeters (30 inches by 30 inches). The visible energy produced by such a light source 14 is "white," including energy in green wavelengths that is in proportion to the energy in other visible wavelengths.

In another embodiment where the wood piece 8 is a board, two 1000 Watt broad spectrum stage lights are mounted about 1.8 meters (six feet) away from the face 30 of the board at 40 degree angle off the axis perpendicular to the face 30 of the board to reduce reflections and provide a fairly uniform illumination over a 0.6 meters square (two foot square) area of the board face 30.

Skilled persons will appreciate that different lighting techniques can be employed to accommodate different image acquisition hardware 16. If a line scan camera is employed, the light source 14 should be bright enough in the green portion of the visible spectrum, for example, to provide for successful image integration. In another example, a strobe light source 14 is employed to control the camera's acquisition of the image instead of depending entirely on a camera's electronic shutter mode. Such light source should also generate sufficient light in the green wavelengths of the visible spectrum to acquire a successful image for processing. Skilled persons will appreciate that green laser or other coherent light sources 14 can be employed and may be preferred when the costs of such embodiments become comparable to the costs of more typical light sources such as those discussed above.

Process blocks 112a and 112b may employ camera interface hardware 18 that preferably resides in a computer 20 and may be a circuit board or card that captures the resulting image from the image acquisition hardware 16 for analysis in the computer 20 and that may also control activation of image data acquisition and/or strobe light timing. Such a circuit board is often referred to as a "frame grabber," is commercially available, and may be located in the computer's system bus. Preferred functions of such card include the capability to properly exercise real-time imaging functions of the image acquisition hardware 16, capture the resulting image data, and present the data to the computer 20 for analysis. For some embodiments, such a card is preferably capable of receiving an external signal to initiate each image capture, and then triggering the strobe and camera to initiate image capture.

Skilled persons will appreciate that if a different kind of camera is used, the camera interface hardware 18 will be changed appropriately. For example, if the image acquisition hardware 16 were a line scan device, then the camera interface hardware 18 would collect image data in single scanned lines and present the data to the computer 20 for assembly into an array image for evaluation. Skilled persons will also appreciate that such card may facilitate only the data collection process and not control the camera. Another example can use a camera containing its own acquisition software and hardware, whereby the data is subsequently transmitted to the computer 20 via a serial communication link such as USB or Fire Wire, requiring no special hardware to be installed in the computer 20.

Skilled persons will appreciate that camera interface hardware 18 may reside in image acquisition hardware 16 or in the personal computer or may be an independent device that is directly or indirectly interfaced to the image acquisition hardware 16 and/or the computer 20. As cameras and computers 20 are continuing to evolve and take on a more complete roles to ease integration, many or all of the functions camera interface hardware 18 will be incorporated into the image acquisition hardware 16, such that a high-speed communication port in the computer's motherboard will accept the data directly from the image acquisition hardware 16 so separate camera interface hardware 18 may be omitted entirely.

In some embodiments, computer 20 may be an off-the-shelf personal computer (PC) with commercially available hardware and software components. Such a computer 20 may have typical attributes, such as a processor speed of 2 to 3 gigahertz, minimum RAM memory 512 megabytes, hard disk, CD drive, keyboard (kbd), mouse, color monitor, Ethernet network card, Microsoft Windows operating system, an interface hardware card, and commercially available and/or customized image processing software and other application(s).

In accordance with process block 114a, the computer 20 processes the image data collected from the image acquisition hardware 16 associated with station 12, and in accordance with process blocks 116 and 118 then communicates the results via an Ethernet connection to other stations 42, production line equipment, an automated processing system (APS), and/or possibly other computers. The connections between the various components and stations can take on many forms, the most common being coaxial cable or shielded twisted paired cables. In addition, the communication medium could be via fiber optic (light energy) or radio frequency. The types of connections used may depend on the proposed communication method desired and the ability to integrate with preexisting components of older wood processing systems, and numerous specific embodiments could be implemented.

The computer hardware employed is expected to be changed over time to incorporate higher speed components and interface devices, as well as increased memory capacity when appropriate as improved components become available. For example, an Ethernet 100/10 Base T network can be replaced by a Gigabit Network or other serial or parallel networks. These communication interfaces can also be integrated into the computer's motherboard, eliminating the need for adding a separate card for the communication function. Fiber optic or radio frequency mediums are also potential methods for this function. The computer 20 is connected to a power source that is preferably protected from voltage or current fluctuations. The image acquisition hardware 16 and light sources 14 may be connected to the same power source as the computer 20 or may be connected to separate power sources.

With the same or different sensors and image processing equipment, the automated processing system examines each piece of wood 8 to determine the most beneficial use of each piece of wood 8, such as grade and dimension, and to provide the corresponding processing instructions, such as where to cut. Such examination may be accomplished concurrently with characterization for identification, or such examination may occur before or after ID characterization or at a separate location. Conventional automated processing systems may employ some or all of the techniques disclosed in any one of U.S. Pat. Nos. 6,757,058; 6,756,789; 5,703,960; 5,644,392; 5,524,771; 5,412,220; 5,254,859; 5,252,836; 4,992,949; 4,926,350; 4,916,629; 4,879,752; 4,867,213; 4,831,545; 4,827,142; 4,606, 654; 4,301,373; 4,286,880; 4,221,974; 4,207,472; 4,086,496; or combinations thereof. The scanning and analytical techniques disclosed in these patents are herein incorporated by reference.

With reference again to FIGS. 1–4, an identification station 42 that is later or downstream of the characterization station 12 may employ types and embodiments of light source(s) 14, image acquisition hardware 16, camera interface hardware 18, and/or computer(s) 20 that are identical to, or different from, those employed in the previous station 12. Skilled persons will appreciate that in most cases identical types and embodiments of these components are preferred to facilitate ease in matching the image data of wood surface characteristics obtained at stations 12 and 42.

An image may be captured of an entire surface or from only a specific area on the piece of wood 8 at both stations 12 and 42, and/or identification station 42 may capture fewer and/or smaller images of portions of wood pieces 8 than those captured at the characterization station 12. Skilled persons will appreciate that if station 12 obtains image data from both of the opposite surfaces of each piece of wood 8, then station 42 will preferably obtain image data from only one of the opposite surfaces in order to establish a match. In some embodiments, pieces of wood travel through station 42 in an intentionally different orientation than the orientation in which they travel through station 12. For example, instead of lineal travel through stations 12 and 42, pieces of wood 8 may have their major axis oriented transversely to, and preferably perpendicularly to, direction of travel 6 at one or both stations 12 and 42. Skilled persons will also appreciate that transverse travel speeds may be different from lineal travel speeds.

Preferred embodiments employ a computer 20 at each downstream identification station 42. Each computer 20 is preferably capable of performing the same tasks concerning collecting image data of wood surface characteristics from its respective image acquisition hardware, with either computer 20 being able to make the final comparison decision. Alternatively, downstream computers 20 may be adapted to perform only some or all of the image characterization, but leave the comparison processing to a central computer (not shown) or a computer 20 at a previous station. The computers 20 preferably communicate with each other and the automated processing system via an Ethernet or other high-speed communication network such as those described above.

Skilled person will appreciate that a single high-speed computer 20 may perform the image characterization and comparison tasks associated with two or more stations 12 and 42. Such a computer 20 would preferably contain the camera interface hardware for the image acquisition hardware of each station 12 and 42 and would be configured to multitask between the demands of each. Some pre-existing wood processing systems already have, for example, a complete scanning system in place that includes its own light sources 14, cameras, and computers 20 with a software architecture that facilitates image acquisition in one computer, image processing in another, decision logic in a third, and communication to the production equipment in another. Skilled persons will also appreciate that the image data collection, processing, and decision process can be implemented in multiple computers 20 that are remote from the stations 12 or 42 where the image acquisition hardware is located. Skilled persons will further appreciate that station 42 may be at a remote location from station 12 such as a separate milling site or customer plant with data sent over the internet or other means, and station 42 may be operated shortly after or at a much later time from when station 12 acquires the image data of a wood piece 8. The physical location and configurations of the data collection and processing hardware can be varied greatly so long as such implementations are reliable and facilitate and desirable processing and communication tasks and speeds.

When a computer 20 receives an image from the image acquisition hardware 16, the image and/or data associated with it may be stored in a circular buffer by software running in the computer 20 at least until the image data is received and/or acknowledged by the respective decisions block 120a or 120b of the image processing hardware. Customized image processing algorithms may be employed to analyze image data with various data manipulation techniques. Such software is preferably adapted to operate in the Windows™ environment and integrate with communication applications in order to share data and results with other computers 20. The software is preferably adapted to take advantage of Intel's Image Processing Library (IPL), Integrated Performance Primitives (IPP), and/or other available libraries that feature specialized software routines that take advantage of specific processing hardware of the computer 20. One advantage of using these libraries is speed. A function call to an IPL routine typically runs much faster than improvised dedicated C++ code. In one embodiment where the wood pieces 8 are boards, the image processing software includes C++ libraries and/or Visual Basic® OCX/DLL software provided by a company called Imaging Control of Charlotte, N.C. Another software application resident in the computer 20 moves the image out of the buffer to a separate memory location so it can be easily accessed by the image processing software.

The software is preferably adapted to perform one or more of the following applications, more preferably two or more of these applications, and most preferably all of these applications: image warping; Fast Fourier Transformation and/or other transformation techniques such as wavelet analysis; interim solution communication; woodprint matching; and/or final solution communication. A description of each of these applications is described below.

With reference to process blocks 114a and 114b, image warping addresses differences between the images taken by the image acquisition hardware 16 at each station 12 or 42. Such differences include, but are not limited to: the position of where each piece of wood 8 ends up in the field of view; resolution differences between the individual image acquisition hardware 16 at different stations 12 and 42; and image contrast. The software will take the image received from the image acquisition hardware 16 and scale it to correspond to a predetermined pixel/inch value in accordance with process blocks 124a and 124b. The software will also adjust the orientation of the piece of wood's image to compensate for any skewing or offset in accordance with process blocks 122*a* and 122*b*. The scaling and orientation adjustments can be done in either order. A calibration procedure at installation using a target with known size and orientation defines the reference points and adjusts for differences in focus, pixel size, lighting, and skew using a calibration target with known size, orientation, and/or other features.

In an exemplary system, where the images taken at stations 12 and 42 are adapted to be appear as similar as possible, the focus, illumination, and spatial alignment are precisely adjusted. Such calibration can be entirely manual or can be partially automated. In an exemplary calibration process for such a system where the piece of wood 8 is a board, after the camera and light sources are mounted, a calibration target is placed under the camera. This target may be a board with lines drawn on it using a green or black marker that border a region of interest. The camera is placed in a mode that makes it continually acquire images. The focus, aperture, and speed (acquisition time) are adjusted to produce a clear image. The position of the camera is then manually adjusted at both stations 12 and 42 so that the cameras produce nearly identical images. Focus is readjusted as needed.

In an exemplary image warping application that addresses scaling wherein the wood piece 8 is a board, the computer software thresholds multiple (or each) horizontal video lines across the image to find the edges of sides 32 of the board. The data from the longest lines (representing the widest part of the board) are used in a least-squares fit calculation to create an artificial border that represents the edges of the board. Using the longest lines helps eliminate areas of missing wood and dark fiber that can make the board appear narrow. The calculation results in a border rectangle that corresponds to the edges of the board and the portion of the field of view that was calibrated for both stations 12 and 42. The image is then scaled to a size compatible to both stations 12 and 42 using a bi-linear transformation. The area within the border rectangle is next divided into two grids: a fine grid and a coarse grid. In an example employing a 25.4-cm (ten-inch) wide board, the fine grid comprises 100 rectangles or cells and the coarse grid comprises 25 rectangles or cells. In some embodiments, each fine cell may, for example, represent a 64×64 camera pixel area.

In an exemplary image analysis process, each cell may be represented by a set of values determined by a Fast Fourier Transform algorithm in accordance with process blocks 126*a* and 126*b*. Exemplary values of interest include the most often found frequency in a grain pattern or growth ring pattern, a representation of such frequency's energy or abundance (magnitude of predominant spatial frequency) compared to those of any other frequencies, and an indication of the grain direction and/or grain direction confidence. Other inherent wood characteristics that may be evaluated include, but are not limited to, contrast, density (as obtained by radio wave or x-ray analysis), or wane characteristics.

Values describing two or more of these features are determined for each cell within both the fine and course grids of the image. Two currently preferred values are grain direction and magnitude of its spatial frequency because these values tend to be fairly insensitive to light intensity and contrast. The actual numbers resulting from the transformation may then be thresholded dynamically to compensate for brightness differences between stations 12 and 42, if desirable. In one example, both grain direction and predominant spatial frequency are allocated numbers between 0 and 255. The collection of the resulting numbers for some or all of the cells for each piece of wood 8 is called a vector file or "image packet."

Other well-known transformation methods such as wavelet analysis may additionally or alternatively be utilized to render the image data. Some examples of wavelet transforms and their use in image storage and analysis are described in detail in U.S. Pat. No. 5,710,835, the description of which is herein incorporated by reference.

These techniques take advantage of grain patterns of wood, which like human fingerprints are unique to each individual. In accordance with process blocks 128*a* and 128*b*, additional imaging, filtering, and analytical techniques can also be employed for identifying repeating or non-repeating features of each piece of wood 8 and/or modifying image packet for the purpose of characterizing and later identifying a piece of wood 8. These include any characteristics captured or analyzed by the automated processing system or characteristics scanned and analyzed as disclosed in any one of U.S. Pat. Nos. 6,757,058; 6,756,789; 5,703,960; 5,644,392; 5,524,771; 5,412,220; 5,254,859; 5,252,836; 4,992,949; 4,926,350; 4,916,629; 4,879,752; 4,867,213; 4,831,545; 4,827,142; 4,606,654; 4,301,373; 4,286,880; 4,221,974; 4,207,472; 4,086,496; or combinations thereof.

In accordance with process blocks 116 and 118, the image packets are sent to the automated processing system and associated with a wood piece number and sent to the computer 20 that will later perform the identification comparison. In some particular embodiments, the image packets may be save in a first-in/first-out (FIFO) packet queue before they are associated with a wood piece number as indicated in process block 130. The interim solution communication involves the destination and application(s) for the image data once it has been transformed to an image packet. Typically, an image packet's destination will be determined by which station 12 or 42 collected the image. If the image data is collected by a station 12 and an initial characterization image packet is created, a sequential wood piece number (WPN) or code is assigned to the image packet, and the information is sent to a computer 20 in communication with a downstream station 42 via the Ethernet connection in accordance with process block 116. In accordance with process block 118, the wood piece number is also made available to the automated processing system so it can relate the wood piece number to its own information about the piece of wood 8. Alternatively, skilled persons will appreciate that the wood piece number could be generated by the automated processing system and communicated to station 12.

In accordance with decision block 140, the computer 20 associated with station 42 waits to receive the characterization image packet and may store it in a buffer memory in a sequential queue of image packets as indicated in process block 142 to associate it with a wood piece number. In a particular embodiment with reference to FIG. 3, the software at one of the computers 20 waits to receive a wood piece number from the automated processing system in accordance with decision block 150 and saves the wood piece number in a first-in/first-out queue in accordance with process block 152. In accordance with a decision block 154, the software then checks whether a reset has been received from the automated processing system or an operator keyboard. If a reset has been received, then the wood piece number first-in/first-out queue may be reset to zero in accordance with process block 156. If no wood piece number reset is indicated, then the software checks for an image packet reset from the automated processing system or an operator keyboard as indicated in decision block 158. If a reset is indicated, then the image packet queue may be reset to zero as indicated in process block 160. If no reset is indicated, then the software checks to determine whether an image packet is available in accordance with decision block 162.

If an image packet is available, the software confirms in accordance with decision block 164 that a valid wood piece number is available, and if so, the software assigns the wood piece number from process block 152 to the image packet from process block 130 in accordance with process block 166. The software also transmits the wood piece number to the automated process system and increments the wood piece number queue. Finally, in accordance with process block 168, the software transmits the wood piece number and the image packet to the computer 20 at station 42 and increments the image packet queue.

If the image packet is collected at station 42 and a downstream or identification image packet is created, the software proceeds with woodprint matching in accordance with process block 144. In one embodiment, the software at a downstream computer checks to determine whether a wood piece number and image packet have been received from station 12 in accordance with decision block 170 and saves this data to a first-in/first out packet queue in accordance with process block 172. Then the software checks for a reset from the automated processing system of an operator keyboard in accordance with process block 174. A reset is performed if indicated in accordance with process block 176, or the upstream characterization image packet is compared to a downstream identification packet as described later in greater detail.

The downstream image packet is then compared to the available characterization image packets in memory to find a match. The wood piece number and its location in memory allow the software to search forward and backward in a logical fashion to look for the image packets of pieces of wood 8 where they are most likely to be, and then widen so as to find those that have moved out of order. Initial image packets concerning pieces of wood 8 whose identities have already been confirmed by the downstream station 42 can be tagged accordingly or discarded so they do not have to be compared. The matching comparison preferably uses a weighted statistical method to compare a downstream image packet to initial image packets in memory. Typically two or more data values for each cell of an image are compared to corresponding data values of cells in an image packet in memory to look for the numbers to match within a predetermined tolerance. If enough matches are successful for a specified number of cells, a successful piece of wood identity is assumed. If there are not enough matches, then the next image packet in memory is considered. This process continues until a match is found, a time limit is reached, or the availability of untested initial image packets is exhausted.

In one embodiment, the comparison process may be driven by the expected flow of wood pieces 8. If the wood pieces 8 are expected to stay in order as they travel from one station 12 to one station 42, then it may be reasonable to only confirm that the wood piece 8 arriving at the identification station 42 is the expected wood piece 8. In a rudimentary embodiment, a simple accept/reject decision might be sufficient and may be obtained by thresholding the results, and a reject result might be sent directly to the automated processing system in accordance with process block 184a and/or examination or intervention by an operator might be requested.

An exemplary image packet comparison technique described below employs a cell-by-cell comparison scheme that awards points in accordance with the cell test results. The grain direction number from a specific cell derived from the image taken at station 12 is compared to the corresponding cell derived from the image taken at station 42. If the numbers match within a very tight tolerance, such as ±1 or up to ±5, then 3 points are awarded for the test, for example. If they match within a wider tolerance, such as +6–10, then 2 points are awarded, for example, etc. The numbers representing the magnitudes of the spatial frequencies or other wood piece characteristics can be similarly evaluated.

If multiple tests, such as for grain direction and frequency magnitude, for a cell achieve 2 or more points, for example, an additional point can be awarded to the cell score. Furthermore, if adjacent cell scores are high, an additional point can be added to the cell score. If the number or vector values of individual cells are low because the original image had very little grain contrast or the imaged area was very irregular, the scores for these cells could also be increased to increase their importance. The total cell scores for each image packet can then be normalized to a 100% scale. The host computer 20 uses the normalized test cell scores to determine if the piece of wood 8 is indeed the same piece of wood seen at both stations 12 and 42. In one embodiment, the normalized test cell scores are converted to an overall confidence level for the piece of wood 8 being identified, and such confidence level may also be affected by the confidence level of the pieces of wood 8 that surround the piece of wood being identified.

In more advanced embodiments, the process may be designed to automatically recover from a problem. For example, if the identification image packet of the wood piece 8 undergoing identification does not present a high confidence match to the image packet of the expected wood piece 8, then the software may check for the presence of additional image packets in accordance with decision block 186, and an image packet for an opposite or other surface of the expected wood piece 8 may be compared to the identification image packet. If a high confidence match is still not found, then it is possible that the piece of wood 8 may have gotten out of position by trading places with its neighbor. Then the software may check for the presence of additional image packets in accordance with decision block 186, so a comparison can be done between the expected wood piece's image packet and its neighbor's image packet(s). These multiple-comparison results could be then further compared using probability techniques well known to skilled practitioners to compensate for process particulars. For example, the software may look for and react to changes in confidence level patterns.

Skilled persons will appreciate that each piece of wood 8 may be associated with two or more image packets if separate packets are desired for each opposite surface or for each face, side, and/or end surface or that each piece of wood 8 may be associated with a single image packet containing characteristic image data for some or all of the wood's surfaces for which an image is collected. The additional image packets associated with each piece of wood 8 can be used for comparison before the image packets concerning other pieces of wood 8 are compared to allow for possibilities of a piece of wood being turned over in its travel between stations 12 and 42. Skilled persons will appreciate that initial and downstream image packets may include data from one or more entire surfaces of a piece of wood 8 or from only portions of one or more surfaces. In some embodiments, stations 12 convert larger portions of wood piece surface images into image packets and stations 42 convert smaller portions of wood piece surface images a into image packets. Preferred minimum areas converted into image packets should have sufficient size to reduce inaccurate identifications.

Once a match is, or is not, found, in accordance with decision blocks 180*a* and 180*b,* the final solution communication involves making the information available to the automated process system. A successful match is signaled by presenting the matching sequential board number to the automated processing system via Ethernet connection in accordance with process blocks 182*a* and 182*b.* A non-match is communicated by presenting a specific failure code in accordance with process blocks 184*a* and 184*b.* Additional algorithms can be used to complement those described. Some wood piece surfaces will be darker or offer less contrast. Sometimes these can be enhanced using additional filtering methods. It may be desirable to modify the image processing algorithms by adding other filtering techniques in order to make the system more robust to accommodate such variables. Additional camera types and image acquisition hardware configurations at both stations 12 and 42 can be implemented along with modifications for processing the image data.

For example, if the data collected by the image acquisition hardware 16 is presented to the computer 20 or its image collection hardware 18 in a manner inconsistent with existing equipment and processing software, the image processing software can be adapted to integrate with it. As computers continue to evolve, there will be more options available for image processing, communication, and other software tasks. Skilled persons will appreciate that the software will evolve with the computer platform hardware as the resulting architecture or speed and memory enhancements make other software techniques favorable.

In some embodiments, all or major portions of the image processing software reside in a single computer 20. In other embodiments, all or major portions of the image processing software reside in each computer 20. In yet other embodiments, specific image processing tasks may be allocated to specific computers 20 or spread out over multiple computers 20. In a further embodiment, some computers 20 may contain all or major portions of the image processing software while other computers 20 may perform only minor tasks. Another specific example includes taking the image acquisition and processing tasks that would be done in station 12 and integrating them into a scanning system that acquires wood piece images for other purposes. The scanning system would produce the image packet information along with its own tasks and either keep such information for later comparison to the downstream identification images, or pass the image packets along to station 42 with a sequential wood piece number.

In systems with a single computer 20, the image acquisition hardware 16 from both stations 12 and 42 are connected directly or indirectly to the computer 20 and processed with the image processing software installed on the computer 20. This computer 20 would also be connected to the production equipment and possibly other computers 20. Additional cabling configurations are possible that connect the computer 20 with a separate image collection/processing system.

In addition, preferred embodiments employ quality control components that can be incorporated into or communicate with pre-existing active self-checking capabilities of existing systems, such that if the system fails, very few boards could pass before a problem is discovered.

An exemplary application of the board print™ technology is described below in the context of a system used to automatically grade wood pieces 8 in a planer mill. The wood pieces 8 are graded boards that vary in thickness and width from 2.5×10 centimeters to 5×30 centimeters (1×4 inches to 2×12 inches) and vary in length from 2.4 to 6 meters (8 to 20 feet) long. The boards are kiln dried and pass through a grading system during the planning, trimming, and sorting process. The boards travel through a planer at lineal speeds averaging 47 meters/minute (1800 feet/min.), immediately pass through the grading scanner, and land on a deck from where chains transport the boards as they are oriented in a transverse direction. At this stage in the process, the boards are not completely controlled, and do not necessarily stay in queue. After a few seconds, the boards are physically separated into individual sections on a lugged chain. It is then desirable to match a board identity with the information collected at the grading scanner because the board will next be trimmed and sorted into a package by automated equipment. Accordingly, a station 42 is preferably located at a position where boards can be identified before they are trimmed and sorted.

When a board passes through the grading scanner, several small halogen lamps and line scan cameras collect image data for the top and bottom wide faces 30 of the board. The data is collected by one or more of a set of computers 20 containing hardware and software for controlling the acquisition and data collection process, and the board is assigned a sequential board number. The primary use of the image data is for grading the board, however, a portion of the image data is also processed in the computer 20 for its board print™ information. This means that the data be warped for size and orientation, FFT values will be generated, the resulting data will be adjusted to compensate for brightness; and the data will be placed in the vector image packet. The image packet is then sent to a host computer 20 where it is stored for the matching process later. This image packet contains information for both the top and bottom wide faces 30 of the board, plus the sequential board number. The sequence number and image data for this board is sent to one of the computers 20, each computer 20 preferably containing the same hardware and software dedicated to image processing. The next board that is scanned will be assigned the next number in sequence and its image data is passed to another one of the computers 20.

After the board finally gets singulated onto the lugged chain, the automatic processing system controlling the production line activates a camera at the identification station 42 and an image is acquired of the top face 30 of the board, which may be oriented transversely to the direction of travel 6. The camera sends the image data via Fire Wire serial format to an external conversion device where the signal is converted to a fiber optic medium and sent to a dedicated board print™ computer 20. When it arrives at the computer 20, external hardware converts the data back to Fire Wire serial format and stores the information in a circular buffer. Software in the computer 20 pulls it out of the buffer and processes it as previously described with an additional step of reorienting the image. Then, the computer 20 relays the data to the host computer 20 via an Ethernet connection for the comparison as previously described.

The host computer 20 compares the vector image packet just received from the station 42 with the image packets from eleven boards for example, such as five boards in the queue ahead of this board, and five boards after this board. Comparison steps are employed as previously described except as modified by the specific embodiment hereinafter described.

Once the comparison scores are generated, the host computer 20 performs the following tasks. If the board score for the expected match is equal or higher than the scores for the adjacent boards, it is considered a match. If the board score for the expected match is up to 20% lower than the scores for any adjacent boards, then the board is considered a match. However, a probability weighting may require that the next board have at least a 10% higher score than that of adjacent boards or be rejected. If the board score for the expected match is more than 20% lower than scores for the adjacent boards, the board is rejected. Once three boards are rejected in a row, the program will automatically adjust to realign the queue. The software does this using data from the last three board comparisons to determine whether there is a trend for one specific board position that is higher than or equal to the scores for adjacent boards as described above. If no trend can be detected in the ten adjacent positions, the host computer 20 instructs the automatic processing system to stop the material flow so the boards can be manually sorted by an operator.

Once an identity decision is made, the host computer 20 transmits the corresponding sequential number and relevant process information (grade and trim decision) to the automatic processing system so it can trim and sort the board accordingly.

In yet another embodiment, a grading system or the automated processing system determines a cutting solution for the pieces of wood 8 that recommends the they be cut into multiple smaller pieces of wood. The image characterization system collects or sorts image data such that an image packet is created for each of the forecast smaller pieces. Skilled person will appreciate that some embodiments may not provide image packets for forecast pieces of wood 8 resulting from internal cuts. An identification station can creates image packets for the recommended multiple smaller pieces of wood after they are cut to confirm the identify of some or all of them.

Skilled persons will appreciate that variations in size, materials, shape, form, function, manner of operation, assembly, and use may impact optimum dimensional and positioning relationships, hardware components, software applications, and system connectivity.

It will be obvious to those having skill in the art that many changes may be made to the details of the above-described embodiments without departing from the underlying principles of the invention. The scope of the present invention should, therefore, be determined only by the following claims.

The invention claimed is:

1. A method for tracking multiple pieces of wood in a wood processing system, comprising:
   obtaining first inherent wood characteristic information from first and second pieces of wood as they move in a first order of a first queue through a first station;
   associating the first inherent wood characteristic information from the first and second pieces of wood with first respective sequential queue positions in the first queue in which the first inherent wood characteristic information is obtained;
   obtaining second inherent wood characteristic information from the first and second pieces of wood in a second order of a second queue at a second station, the second order being the same as or different from in the first order;
   associating the second inherent wood characteristic information from the first and second pieces of wood with second respective sequential queue positions in the second queue in which the second inherent wood characteristic information is obtained; and
   comparing the second inherent wood characteristic information of a given first or second piece of wood associated with a primary queue position within the second queue to the first inherent wood characteristic information of a given first or second piece of wood associated with a corresponding primary queue position within the first queue to make an evaluation of similarity between the first and second inherent wood characteristic information associated with the corresponding primary queue positions.

2. The method of claim 1 in which the first and second pieces of wood each have a surface and the inherent wood characteristic information is obtained from the surface.

3. The method of claim 1 in which the first and second pieces of wood each have at least first and second surfaces and the inherent wood characteristic information is obtained from both the first and second surfaces.

4. The method of claim 3 in which the inherent wood characteristic information of only either one of the first or second surfaces of the piece of wood is obtained at the second station to uniquely identify the piece of wood.

5. The method of claim 1 in which obtaining the wood surface characteristic information further comprises obtaining an image of at least a portion of the first and second pieces of wood.

6. The method of claim 1 in which the wood surface characteristic information comprises a grain characteristic.

7. The method of claim 6 in which the grain characteristic comprises grain frequency magnitude, grain direction, and/or grain direction confidence.

8. The method of claim 1 in which the wood surface characteristic information comprises tracheid data.

9. The method of claim 1 in which the first and second pieces of wood comprise at least one of the following: timber, lumber, log, fitch, cant, beam, post, stud, or board.

10. The method of claim 1 in which the first and second pieces of wood are surfaced or unsurfaced.

11. The method of claim 1 in which the first and second pieces of wood comprise any level of moisture content within the range of uncured to cured.

12. The method of claim 1 in which the first and second pieces of wood each comprise a board and the inherent wood characteristic information comprises a defect.

13. The method of claim 12 in which the defect comprises at least one of bark, missing wood, or a physical shape defect.

14. The method of claim 13 in which the physical shape defect comprises a wane defect.

15. The method of claim 1 in which the first and second pieces of wood each comprise a board and the inherent wood characteristic information is obtained from an end, side, or face of the board.

16. The method of claim 1 in which the inherent wood characteristic information is obtained with different types of first and second image acquisition hardware at the respective first and second stations, and at least one of the first or second image acquisition hardware comprises a camera.

17. The method of claim 1 in further comprising:
obtaining the first inherent wood characteristic information from first and second pieces of wood traveling in a first orientation through the first station; and
obtaining the second inherent wood characteristic information from the first and second pieces of wood traveling in a second orientation through the second station, the second orientation being intentionally transverse to the first orientation.

18. The method of claim 1 in further comprising: obtaining the first inherent wood characteristic information from first and second pieces of wood traveling at a first travel speed through the first station; and
obtaining the second inherent wood characteristic information from the first and second pieces of wood traveling at a second travel speed through the second station, the second travel speed being different from the first travel speed.

19. The method of claim 1 further comprising employing different types of light sources at the first and second stations to illuminate the pieces of wood as their inherent wood characteristic information is obtained.

20. The method of claim 19 in which at least one of the light sources is pulsed or strobed.

21. The method of claim 19 in which at least one of the light sources presents a light line.

22. The method of claim 19 in which the inherent wood characteristic information associated with a green wavelength is detected or analyzed independently.

23. The method of claim 1 further comprising exposing the pieces of wood to x-ray radiation to facilitate obtaining their inherent wood characteristic information.

24. The method of claim 1 further comprising exposing the pieces of wood to radio waves to facilitate obtaining their inherent wood characteristic information.

25. The method of claim 1 in which the wood surface characteristic information is obtained in cooperation with a wood grading system.

26. The method of claim 1 in which the inherent wood characteristic information is obtained from a wood surface of an intended appearance-grade product.

27. The method of claim 1 further comprising:
associating the inherent wood characteristic information from the first and second pieces of wood with respective confidence values; and
using the confidence values associated with the inherent wood characteristic information obtained at the first station to confirm the identify of the first and second pieces of wood at the second station.

28. The method of claim 1 in which the evaluation of similarity between the first and second inherent wood characteristic information determines whether there is a match within predetermined statistical parameters between the first and second inherent wood characteristic information associated with the corresponding primary queue positions.

29. The method of claim 1 further comprising:
converting the first inherent wood characteristic information of the first and second pieces of wood into respective first data packets that are associated with the first respective sequential queue positions;
converting the second inherent wood characteristic information of the first and second pieces of wood into respective second data packets that are associated with the second respective sequential queue positions; and
comparing the second data packet of the given first or second piece of wood associated with the primary queue position within the second queue to the first data packet of the given first or second piece of wood associated with the corresponding primary queue position within the first queue to determine whether the first and second inherent wood characteristic information associated with the corresponding primary queue positions constitutes a match within predetermined statistical parameters.

30. The method of claim 29 in which the comparisons are performed by a central computer.

31. The method of claim 30 in which the comparisons are performed by a computer associated with the second station.

32. The method of claim 29 in which obtaining inherent wood characteristic information further comprises:
obtaining an image from a portion of respective surfaces of the first and second pieces of wood at both stations; and
independently adjusting images of the respective surfaces of the first and second pieces of wood at both stations to conform to a predetermined size and orientation.

33. The method of claim 32, further comprising:
characterizing the images with a Fast Fourier Transformation technique.

34. The method of claim 32, further comprising:
dividing each image into a corresponding array of image portion cells;
characterizing the inherent wood characteristic information within the image portion cells with a Fast Fourier Transformation technique to provide for some or all of the cells at least one value for the inherent wood characteristic information; and
comparing the values of corresponding cells of respective images to determine whether a sufficient number of corresponding cells have sufficiently similar values to be presented as a match or sufficiently different values to be presented as a nonmatch.

35. The method of claim 1 further comprising:
cutting the first piece of wood into at least third and fourth pieces of wood; and
using the inherent wood characteristic information obtained at the first station to confirm the identify of at least the third or the fourth pieces of wood.

36. The method of claim 1 in which a cutting solution is determined for the first piece of wood that recommends the first piece of wood be cut into multiple smaller pieces of wood and in which inherent wood characteristic information is obtained for some of the recommended multiple smaller pieces of wood, further comprising:
cutting the first piece of wood into at least third and fourth pieces of wood; and
using the inherent wood characteristic information obtained at the first station to confirm the identify of some of the recommended multiple smaller pieces of wood.

37. The method of claim 1 further comprising:
associating with a confidence level the evaluation of similarity between the first and second inherent wood characteristic information associated with the corresponding primary queue positions; and
employing the confidence level concerning the corresponding primary queue positions to determine whether first and second inherent wood characteristic information associated with adjacent corresponding queue positions constitutes a match within predetermined statistical parameters.

38. A wood tracking system, comprising:
- first image acquisition hardware for collecting a first image of at least a first portion of a surface of a piece of wood as it travels across a first image collection area;
- second image acquisition hardware for collecting a second image of at least a second portion of the surface of the piece of wood as it travels across a second image collection area at a different location than the first image collection area, the second portion including some or all of the first portion;
- image processing software adapted for independently adjusting first and second portions of respective first and second images to conform to a predetermined size and orientation;
- image characterization software located on one or more computers for characterizing an inherent wood surface characteristic appearing in the first and second portions of the respective first and second images to create values for the inherent wood surface characteristics within the respective first and second image portions; and
- comparison software located on one or more computers for comparing the values of the inherent wood surface characteristics within the respective first and second image portions and for determining whether the values have sufficient similarities to he presented as a match or sufficient differences to be presented as a nonmatch.

39. The wood tracking system of claim 38 in which multiple pieces of wood travel across the first and second image collection areas, each piece of wood has at least first and second surfaces, and images are obtained from both the first and second surfaces of each piece of wood in proximity to at least one of the image collection areas.

40. The wood tracking system of claim 39 further comprising different types of first and second light sources at the respective first and second image collection areas for illuminating the surface of the piece of wood.

41. The wood tracking system of claim 40 in which at least one of the light sources presents a light line.

42. The wood tracking system of claim 40 in which the inherent wood characteristic information associated with a green wavelength is detected or analyzed independently.

43. The wood tracking system of claim 38 in which the inherent wood surface characteristic comprises a grain characteristic value.

44. The wood tracking system of claim 43 in which the grain characteristic value comprises grain frequency, grain frequency magnitude, grain direction, contrast, and/or grain direction confidence.

45. The wood tracking system of claim 38 in which the inherent wood surface characteristic comprises tracheid data.

46. The wood tracking system of claim 38 in which multiple pieces of wood travel across the first and second image collection areas and the pieces of wood comprise at least one of the following: timber, lumber, log, fitch, cant, beam, post, stud, board, or veneer.

47. The wood tracking system of claim 38 in which multiple pieces of wood travel across the first and second image collection areas and the pieces of wood comprise any level of moisture content within the range of cured to uncured.

48. The wood tracking system of claim 38 in which multiple pieces of wood travel across the first and second image collection areas and the pieces of wood comprise any level of moisture content.

49. The wood tracking system of claim 38 in which multiple pieces of wood travel across the first and second image collection areas and in which the pieces of wood each comprise a board and the inherent wood surface characteristic comprises a defect including one of the following: bark, missing wood, or a twist.

50. The wood tracking system of claim 38 in which multiple pieces of wood travel across the first and second image collection areas and in which the pieces of wood each comprise a board and the inherent wood surface characteristic is obtained from an end, side, or face of the board.

51. The wood tracking system of claim 38 in which the first and second image acquisition hardware are of different types, and at least one of the first or second image acquisition hardware comprises a camera.

52. The wood tracking system of claim 38 in which the inherent wood surface characteristic is obtained in cooperation with a wood grading system.

53. The wood tracking system of claim 38 in which the inherent wood surface characteristic is obtained from a wood surface of an intended appearance-grade product.

54. The wood tracking system of claim 38 in which the first image acquisition hardware collects the first image as the piece of wood travels at a first travel speed through the first image collection area, and in which the second image acquisition hardware collects the second image as the piece of wood travels at a second travel speed through the second image collection area, the second travel speed being different from the first travel speed.

55. The wood tracking system of claim 38 in which the wood surface characteristic information of only either one of the first or second sides of the piece of wood is employed at the second station to uniquely identify the piece of wood.

56. The wood tracking system of claim 38 in which the characterization software employs Fast Fourier Transformation or wavelet analysis.

57. The wood tracking system of claim 38 in which the image acquisition hardware collects radio frequency data.

58. The wood tracking system of claim 38 in which the image processing software, image characterization software, and comparison software are all located on one computer.

59. The wood tracking system of claim 38 in which at least one of the image processing software, image characterization software, or comparison software is located on a computer that is remote from at least one of the image collection areas.

60. The wood tracking system of claim 38 further comprising:
- a cutting station for cutting the piece of wood into at least second and third pieces of wood such that the second portion of the wood piece surface is located on the second or third pieces of wood.

61. The wood tracking system of claim 38 in which a cutting solution is determined for the piece of wood that recommends the piece of wood be cut into multiple smaller pieces of wood and in which inherent wood surface characteristics are characterized for some of the recommended multiple smaller pieces of wood, further comprising:
- a cutting station for cutting the piece of wood into the recommended multiple smaller pieces of wood such that a first image arc obtained from some of the recommended multiple smaller pieces of wood before the piece of wood is cut and such that second images are obtained from some of the recommended multiple smaller pieces of wood after they are cut to confirm the identify of some of the recommended multiple smaller pieces of wood.

62. The wood tracking system of claim 38 in which the first image acquisition hardware collects the first image as the piece of wood travels in a first orientation through the first image collection area, and in which the second image acquisition hardware collects the second image as the piece of wood travels in a second orientation through the second image collection area, the second orientation being intentionally transverse to the first orientation.

63. The wood tracking system of claim 38 in which the first image acquisition hardware is adapted to collect first images of at least portions of respective first and second pieces of wood having first respective sequential queue positions in a first queue in which the first images are obtained, in which the second image acquisition hardware is adapted to collect second images of at least a part of the portions of the respective first and second pieces of wood having second respective sequential queue positions in a second queue in which the second images are obtained, in which the image characterization software converts the first images into respective first data packets associated with the values for the inherent wood characteristic information of the first and second pieces of wood, in which the image characterization software converts the second images into respective second data packets associated with the values for the inherent wood characteristic information of the first and second pieces of wood, in which the first images and/or first data packets are associated with the first respective sequential queue positions, in which the second images and/or second data packets are associated with the second respective sequential queue positions, and in which the comparison software compares the second data packet of the given first or second piece of wood associated with a primary queue position within the second queue to the first data packet of the given first or second piece of wood associated with a corresponding primary queue position within the first queue to determine whether the values for the inherent wood characteristic information associated with the corresponding primary queue positions constitute a match within predetermined statistical parameters.

64. The wood tracking system of claim 63 in which a confidence level is associated with the evaluation of similarity between the first and second inherent wood characteristic information associated with the corresponding primary queue positions, and in which the confidence level concerning the corresponding primary queue positions is employed to determine whether first and second inherent wood characteristic information associated with adjacent corresponding queue positions constitutes a match within predetermined statistical parameters.

65. A method for characterizing a piece of wood, comprising:
capturing a first image of at least a first portion of a surface of each of multiple primary pieces of wood as they travel across a first station;
dividing the first portions into respective similar first virtual arrays of respective multiple first corresponding cells;
assigning for some or all of the first multiple corresponding cells one or more characteristic values based on an inherent wood surface characteristic as it appears in the respective multiple first corresponding cells;
capturing a second image of at least a second portion of a surface of a secondary piece of wood as it travels across a second station, the secondary piece of wood being one of the multiple primary pieces of wood;
dividing the second portion into a second virtual array of multiple second corresponding cells corresponding to respective similar multiple first corresponding cells;
assigning for some or all of the multiple second corresponding cells a characteristic value based on the inherent wood surface characteristic as it appears in the respective multiple second corresponding cells;
comparing the characteristic value of the inherent wood surface characteristic for some or all of the multiple second corresponding cells to the characteristic value of the inherent wood surface characteristic for some or all of the corresponding multiple first corresponding cells associated with any given primary piece of wood; and
determining whether a sufficient number of the respective multiple first and second corresponding cells have sufficiently similar characteristic values to indicate that the secondary piece of wood and the given primary piece of wood are the same or have sufficiently different characteristic values to indicate that the secondary piece of wood and the given primary piece of wood are different.

66. The method of claim 65 in which the first and second images are obtained with different types of first and second image acquisition hardware at the respective first and second stations, and at least one of the first or second image acquisition hardware comprises a camera.

67. The method of claim 65 further comprising:
obtaining the first image from each primary piece of wood as it travels in a first orientation through the first station; and
obtaining the second image from the secondary piece of wood as it travels in a second orientation through the second station, the second orientation being intentionally transverse to the first orientation.

68. The method of claim 65 further comprising:
obtaining the first image from each primary piece of wood as it travels at a first travel speed through the first station; and
obtaining the second image from the secondary piece of wood as it travels at a second travel speed through the second station, the second travel speed being different from the first travel speed.

69. The method of claim 65 further comprising:
associating the characteristic values from the primary pieces of wood with respective confidence values; and
using the confidence values associated with the characteristic values obtained at the first station to confirm the identify of the secondary piece of wood at the second station.

* * * * *